United States Patent [19]

Cantello

[11] 4,409,216
[45] Oct. 11, 1983

[54] METHOD OF TREATING DIABETES USING OXAZOLINE OR THIAZOLINE COMPOUNDS

[75] Inventor: Barrie C. C. Cantello, Redhill, England

[73] Assignee: Beecham Group Limited, England

[21] Appl. No.: 139,284

[22] Filed: Apr. 11, 1980

[30] Foreign Application Priority Data

Apr. 20, 1979 [GB] United Kingdom ............... 7913864

[51] Int. Cl.³ ................. A61K 31/42; A61K 31/425; A61K 31/535; A61K 31/54
[52] U.S. Cl. ................. 424/246; 424/248.51; 424/248.55; 424/248.56; 424/267; 424/250; 424/270; 424/272; 544/58.7; 544/60; 544/62; 544/133; 544/135; 544/137; 544/368; 544/364; 546/198; 546/209; 548/161; 548/193; 548/194; 548/197; 548/198; 548/222; 548/233
[58] Field of Search ............ 544/133, 135, 137, 58.7, 544/60, 62, 368, 369; 546/198, 209; 548/161, 193, 194, 197, 198, 222, 233; 424/248.51, 248.55, 248.56, 250, 270, 272, 246, 267

[56] References Cited

U.S. PATENT DOCUMENTS

| | | | |
|---|---|---|---|
| 3,023,103 | 2/1962 | Dersch et al. | 548/222 |
| 4,089,965 | 5/1978 | Angier et al. | 424/270 |
| 4,250,173 | 2/1981 | Cantello | 548/198 |

FOREIGN PATENT DOCUMENTS 852565 3/1977 Belgium.
1409768 10/1975 United Kingdom.

OTHER PUBLICATIONS

Kurzer et al., *Chem. Abstracts*, vol. 55 (1961), col. 1587c.
Bhargava et al., *Chem. Abstracts*, vol. 69 (1968), No. 77152h.
Chaurasia et al., *Chem. Abstracts*, vol. 71 (1969), No. 112,848e.
Bhargava et al., *Chem. Abstracts*, vol. 72 (1970), No. 88692x.
Bhargava et al., *Chem. Abstracts*, vol. 73 (1970), No. 87,831a.
Bhargava et al., *Chem. Abstracts*, vol. 75 (1971), No. 63678w.
Bhargava et al., *Chem. Abstracts*, vol. 76 (1972), No. 126,880z.
Bhargava et al., *Chem. Abstracts*, vol. 79 (1973), No. 105,127f.
Bhargava et al., *Chem. Abstracts*, vol. 80 (1974), No. 108,419j.
Srivastava et al., *Chem. Abstracts*, vol. 88 (1978), No. 152,476q.
Srivastava et al., *Chem. Abstracts*, vol. 77 (1972), No. 70784x.
Roy et al., *Chem. Abstracts*, vol. 48 (1954), col. 4116h.
Bhargava et al., *Chem. Abstracts*, vol. 76 (1972), No. 72442n.
Choubey, *Current Science*, vol. 40 (1971), pp. 322-323.
Bhargava et al., *Chem. Abstracts*, vol. 76 (1972), No. 14418y.
Srivastava, *J. Chem. Eng. Data*, 1978, vol. 23, pp. 177-178.

*Primary Examiner*—Robert W. Ramsuer
*Attorney, Agent, or Firm*—Jacobs & Jacobs

[57] ABSTRACT

A compound, with hypoglycaemic activity, having formula (II) or a pharmaceutically acceptable acid addition salt thereof:

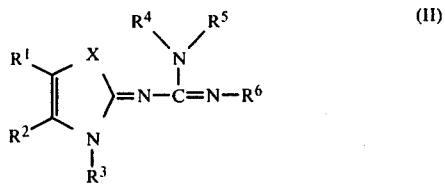

wherein
X represents oxygen or sulphur;
$R^1$ $R^2$ are the same or different and represent hydrogen, halogen, $C_{1-6}$ alkyl, phenyl, benzyl, $C_{3-6}$ cycloalkyl, carbo-$C_{1-6}$ alkoxy or $C_{1-6}$ carboxy or $R^1$ and $R^2$ represent the remaining members of a benzene ring;
$R^3$ represents hydrogen, $C_{1-6}$ alkyl, phenyl or benzyl;
$R^4$ represents hydrogen or $C_{1-6}$ alkyl;
$R^5$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^4$ and $R^5$ together represent the remaining members of a 5- or 6- membered ring optionally containing an oxygen, sulphur or additional nitrogen atom and being optionally substituted with $C_{1-6}$ alkyl; and
$R^6$ represents $C_{1-6}$ alkyl, phenyl, optionally substituted with up to 3 groups selected from halogen, nitro-, amino-, trifluoromethyl, $C_{1-6}$ alkyl and $C_{1-6}$ alkoxy; or benzyl optionally substituted with up to 3 groups selected from halogen, $C_{1-6}$ alkyl and $C_{1-6}$ al

2 Claims, No Drawings

METHOD OF TREATING DIABETES USING OXAZOLINE OR THIAZOLINE COMPOUNDS

This invention relates to a class of novel oxazoline and thiazoline derivatives which are useful in the treatment of diabetes. The invention also relates to processes for their preparation and to pharmaceutical compositions containing them.

The compound of formula (I):

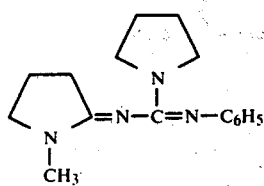

has been reported to be useful in the treatment of diabetes in Belgian Pat. No. 852,565 and in Diabetes, 27, 856 and 868 (1978).

We have found a novel class of oxazoline and thiazoline compounds which have hypoglycaemic activity.

Accordingly the present invention provides a compound of formula (II) or a pharmaceutically acceptable acid addition salt thereof:

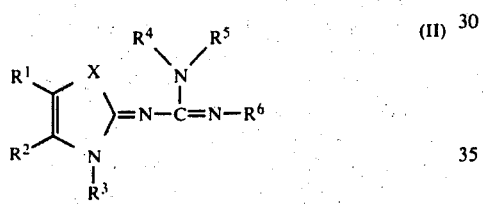

wherein

X represents oxygen or sulphur; $R^1$ and $R^2$ are the same or different and represent hydrogen, halogen, $C_{1-6}$ alkyl, phenyl, benzyl, $C_{3-6}$ cycloalkyl, carbo-$C_{1-6}$ alkoxy or carboxy or $R^1$ and $R^2$ represent the remaining members of a benzene ring;

$R^3$ represents $C_{1-6}$ alkyl, phenyl or benzyl;

$R^4$ represents hydrogen or $C_{1-6}$ alkyl;

$R^5$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^4$ and $R^5$ together represent the remaining members of a 5- or 6-membered ring optionally containing an oxygen, sulphur or additional nitrogen atom and being optionally substituted with $C_{1-6}$ alkyl; and $R^6$ represents $C_{1-6}$ alkyl, phenyl, optionally substituted with up to 3 groups selected from halogen, nitro-, amino-, trifluoromethyl, $C_{1-6}$ alkyl and $C_{1-6}$ alkoxy; or benzyl optionally substituted with up to 3 groups selected from halogen, $C_{1-6}$ alkyl and $C_{1-6}$ alkoxy.

Suitable acid addition salts of compound (II) include inorganic salts such as the sulphate, nitrate, phosphate and borate, hydrohalides such as the hydrochloride, hydrobromide and hydroiodide, and organic acid addition salts such as acetate, oxalate, tartrate, maleate, citrate, succinate, benzoate, ascorbate, methanesulphonate and p-toluenesulphonate.

Preferred salts are hydrohalide salts.

The group X in compounds of formula (II) preferably represents sulphur.

Examples of suitable $C_{1-6}$ alkyl groups which $R^1$ to $R^6$ may represent include methyl, ethyl, n- and iso-propyl, and n-, sec-, iso-, and tert-butyl.

Examples of cycloalkyl groups which $R^1$ and $R^2$ may represent include cyclopentyl and cyclohexyl.

Suitable substituents for the phenyl and benzyl groups for $R^5$ and $R^6$ include ortho-, meta- and para-methyl, methoxy, chloro, bromo, fluoro and nitro.

Suitably $R^1$ and $R^2$ represent hydrogen, methyl, ethyl, or n-propyl or complete a benzene ring.

Preferably $R^1$ and $R^2$ are either hydrogen or methyl.

Suitably $R^3$ is methyl, ethyl, n-propyl, or phenyl, but preferably $R^3$ is methyl.

Suitably $R^4$ is hydrogen, methyl, ethyl or n-propyl, and $R^5$ represents methyl, ethyl, n-propyl, phenyl or benzyl. When $R^4$ and $R^5$ complete a ring, suitable such rings include pyrrolidine, piperidine, morpholine, thiamorpholine, piperazine and 4-methylpiperazine rings. Preferably $R^4$ and $R^5$ are each ethyl or complete a morpholine ring.

Suitably $R^6$ is methyl, ethyl, n-propyl or phenyl, but preferably $R^6$ is phenyl or substituted phenyl.

One sub-group of compounds falling within the scope of this invention comprises compounds of formula (III) and pharmaceutically acceptable acid addition salts thereof:

$$R^7, R^8, S, R^{10}, R^{11}, N, N-C=N-R^{13}, R^9 \quad (III)$$

wherein $R^7$ and $R^8$ represent hydrogen, $C_{1-6}$ alkyl, halogen or carbo-$C_{1-6}$-alkoxy or together form the remaining members of a benzene ring;

$R^9$ represents hydrogen or $C_{1-6}$ alkyl;

$R^{10}$ represents hydrogen or $C_{1-6}$ alkyl;

$R^{11}$ represents $C_{1-6}$ alkyl, optionally substituted phenyl or benzyl; or $R^{10}$ and $R^{11}$ together form the remaining members of a pyrrolidine, morpholine, thiamorpholine or piperidine ring, and $R^{13}$ represents phenyl optionally substituted by halogen or $C_{1-6}$ alkyl.

Preferably, $R^9$ is $C_{1-6}$ alkyl, and $R^{10}$ and $R^{11}$ together form the remaining members of a pyrrolidine or morpholine ring.

Examples of compounds of formula (III) include the following:

N-(3-methylthiazolin-2-ylidene)-N'-phenyl-1-pyrrolidinecarboxamidine; N-(3-methylthiazolin-2-ylidene)-N'-phenyl-4-morpholinecarboxamidine hydroiodide; N-benzyl-N-methyl-N'-(3-methylthiazolin-2-ylidene)-N''-phenylguanidine; N'-(4-methylphenyl)-N-(3-methylthiazolin-2-ylidene)-4-morpholinecarboxamidine hydroiodide; N'-(4-chlorophenyl)-N-(3-methylthiazolin-2-ylidene)-1-pyrrolidinecarboxamidine; N'-(4-chlorophenyl)-N-(3-methylthiazolin-2-ylidene)-4-morpholinecarboxamidine; N-(3-methylthiazolin-2-ylidene)-N'-phenyl-4-thiamorpholinecarboxamidine; N,N-diethyl-N'-(3-methylthiazolin-2-ylidene)-N''-phenylguanidine; N-(3-ethylthiazolin-2-ylidene)-N'-phenyl-4-morpholinecarboxamidine; N-(3,4-dimethylthiazolin-2-ylidene)-N'-phenyl-4-morpholinecarboxamidine; N-(3,5-dimethylthiazolin-2-ylidene)-N'-phenyl-1-pyrrolidinecarboxamidine; N-(3,5-dimethylthiazolin-2-ylidene)-N'-phenyl-4-morpholinecarboxamidine; N'-phenyl-N-(3,4,5-trimethylthiazolin-2-ylidene)-4-morpholinecarboxamide; N-(5-bromo-3-methylthiazolin-2-ylidene)-N'-phenyl-4-morpholinecarboxamidine hydrochloride; N-(3-methylbenzothiazolin-2-ylidene)-N'-phenyl-1-pyrrolidinecarboxamidine; N-(3-methylbenzothiazolin-2-ylidene)-N'-phenyl-4-morpholinecarboxamidine hydrochloride; N-(3-methyloxazolin-2-ylidene)-N'-phenyl-4-morpholine-carboxamidine hydroiodide; N,N-dimethyl-N'-(3-methylthiazolin-2-ylidene)-N''-phenylguanidine hydroiodide; N'-(4-fluorophenyl)-N-(3-methylthiazolin-2-ylidene)-4-morpholinecarboxamidine; N'-(2,6-dichlorophenyl)-N-(3-methylthiazolin-2-ylidene)-4-morpholinecarboxamidine; N-(5-chloro-3-methylthiazolin-2-ylidene)-N'-phenyl-4-morpholinecarboxamidine; N-(4-carboethoxy-3-methylthiazolin-2-ylidene)-N'-phenyl-4-morpholinecarboxamidine.

Compounds of formula (II) may be prepared by reacting a compound of formula (IV) or a salt thereof:

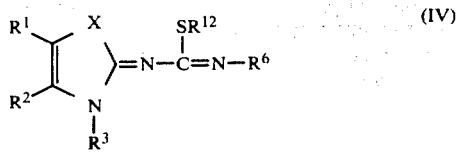

(IV)

wherein $R^1$, $R^2$, $R^3$ and $R^6$ are as defined with respect to formula (II) above, and $R^{12}$ represents $C_{1-6}$ alkyl; with an amine of formula $R^4R^5NH$, wherein $R^4$ and $R^5$ are as defined with reference to formula (II) above and thereafter where desired converting a free base of formula (II) so obtained into a pharmaceutically acceptable salt or converting a salt of a compound of formula (II) so obtained into the free base.

The reaction is conveniently carried out in polar organic solvent, the choice of which is not critical to the success of the reaction provided that it forms a homogeneous solution of the reagent and is substantially inert to the reagent and product. Convenient solvents include alkanols such as iso-propanol and alkanoic acids such as glacial acetic acid.

The reaction is generally carried out at a moderate temperature i.e. greater than room temperature, the reflux temperature of the solvent being selected for convenience.

The period for which the reaction is allowed to proceed depends upon the particular starting materials employed. The course of the reaction may be followed by conventional methods such as thin layer chromatography and terminated when an optimum quantity of product is present in the reaction mixture. However, in general we have found that it is convenient to leave the reaction mixture to reflux overnight.

Intermediates of general formula (IV) are novel and represent a further aspect of the invention.

Examples of $C_{1-6}$ alkyl groups which $R^{12}$ may represent include methyl, ethyl, n-propyl or n-butyl but preferably $R^{12}$ represents methyl.

The intermediates of formula (IV) may be prepared by the route shown in the following scheme:

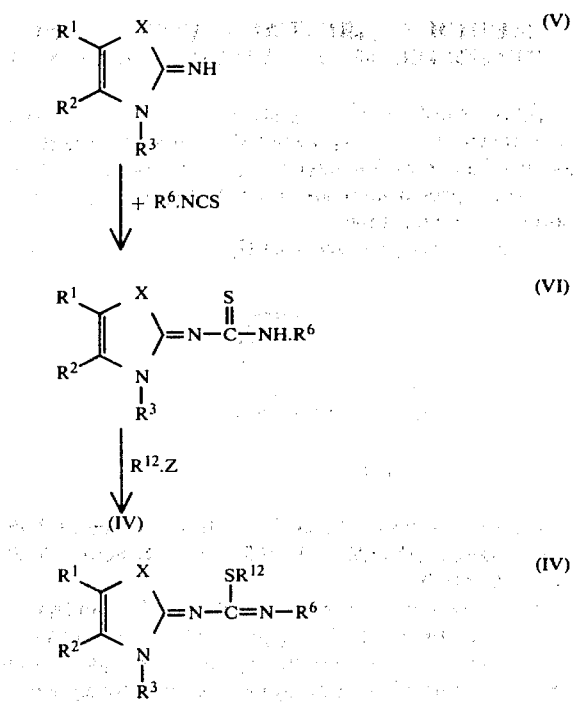

Thus, intermediates (IV) are prepared by alkylation of a thiourea (VI) using an alkylating agent $R^{12}.Z$ wherein $R^{12}$ is as defined with reference to formula (IV) and Z is a leaving group such as chloride, bromide or iodide. Suitably the reaction is carried out in a polar organic solvent, the choice of which is not critical. Suitable solvents include lower alkanones. The reaction is suitably carried out at the boiling point of the solvent.

The thiourea (VI) is in turn prepared by reacting an iso-thiocyanate $R^6.NCS$ with a corresponding imino compound (V), where $R^1$, $R^2$, $R^3$, $R^6$ and X are as defined with reference to formula (II). This reaction is carried out in a solvent such as ethanol, toluene, benzene, dioxane or tetrahydrofuran. The reaction is carried out at non-extreme temperatures i.e. up to and including the reflux temperature of the solvent.

Compounds of formula (II) may also be prepared by reacting a compound of formula (VII):

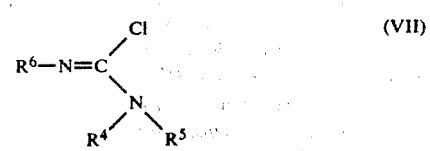

(VII)

wherein $R^4$, $R^5$ and $R^6$ are as defined with respect to formula (II) above; with an imino compound (V), where $R^1$, $R^2$, $R^3$ and X are as defined with respect to formula (II) above and thereafter where desired converting a free base of formula (II) so obtained into a pharmaceutically acceptable salt or converting a salt of a compound of formula (II) so obtained into the free base.

The reaction is conveniently carried out in a solvent system such as an ether, chlorinated hydrocarbon or a mixture thereof. Suitable solvent systems include mixtures of diethyl ether and chloroform. The reaction is suitably carried out at ambient temperature. The period for which the reaction is allowed to proceed may be determined by methods as described hereinbefore; however, we have found it convenient to leave the reaction mixture to stand overnight.

The intermediates of formula (VII) may be prepared by reaction of an isocyanide dichloride of formula: $R^6$—N=CCl$_2$ wherein $R^6$ is as defined with respect to formula (II) above; with an amine of formula $R^4R^5$NH, wherein $R^4$ and $R^5$ are as defined with reference to formula (II) above. Suitably the reaction is carried out in ethereal solvent such as diethyl ether or tetrahydrofuran. The reaction is suitably carried out at ambient temperature. The period for which the reaction is allowed to proceed may vary; however, we have found a two hour reaction time to be sufficient.

In order to put the compounds (II) to use as medicinal agents for the treatment of diabetes, they are presented as pharmaceutical compositions in a variety of dosage forms. This invention therefore also includes a pharmaceutical composition which comprises a compound of formula (II) together with a pharmaceutically acceptable carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, maize-starch, calcium phosphate, sorbitol or glycine; tabletting lubricants, for example magnesium stearate, talc, polyethylene glycol, or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcelluose, carboxy-methyl cellulose, aluminum stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. The compound may also if desired be incorporated in a foodstuff, for example in the form of a biscuit.

For parenteral administration, fluid unit dosage forms are prepared utilizing the compound and a sterile vehicle, and concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. The dosage employed for adult treatment will of course depend on the dose-response characteristics of the particular active ingredient but will normally be in the range 0.1 to 150 mg/kg/day.

The following Examples illustrate the preparation of a number of compounds of this invention:

EXAMPLE 1

N-(3-Methylthiazolin-2-ylidene)-N'-phenyl-1-pyrrolidinecarboxamidine (a) 1-(3-Methylthiazolin-2-ylidene)-3-phenyl-2-thiourea Sodium methoxide (5.40 g) was added to a stirred mixture of 2-imino-3-methylthiazoline hydroiodide (24.95 g) in ethanol (100 ml) and the mixture brought to reflux. Phenyl isothiocyanate (16.35 g) in toluene (50 ml) was added over 30 minutes and reflux continued for a further hour then cooled in ice. The solid obtained on filtration and washing with ethanol and water was dried to give the product, mpt 172.5°–173.5°. Recrystallisation from iso-propanol gave analytically pure product, mpt 173.5°–174°.

(b)
2-Methyl-3-(3-methylthiazolin-2-ylidene)-1-phenyl-2-thiopseudourea hydroiodide A mixture of 1-(3-methylthiazolin-2-ylidene)-3-phenyl-2-thiourea (2.52 g), methyliodide (1.80 g) and acetone (50 ml) was heated under reflux, with stirring, for one hour, cooled in ice and filtered to give analytically pure product, mpt 167°–169°.

(c)
N-(3-Methylthiazolin-2-ylidene)-N'-phenyl-1-pyrrolidinecarboxamidine

A mixture of 2-methyl-3-(3-methylthiazolin-2-ylidene)-1-phenyl-2-thiopseudourea hydroiodide (10.75 g) and pyrrolidine (8.17 g) in dry iso-propanol (85 ml) was heated under reflux for three days, cooled in ice, triturated and filtered to give the product, mpt 123°–124.5°. Recrystallisation from petroleum ether (bp 80°–100°) gave analytically pure product, mpt 125.5°–127°. The hydrochloride salt had mpt 234°–235°.

EXAMPLES 2 AND 3

By an analogous procedure to that described in Example 1(c), the following products were obtained by reaction of 2-methyl-3-(3-methylthiazolin-2-ylidene)-1-phenyl-2-thiopseudourea hydroiodide with the appropriate amine:

EXAMPLE 2

N-(3-Methylthiazolin-2-ylidene)-N'-phenyl-4-morpholinecarboxamidine hydroiodide, mpt 247°–9° (ethanol).

EXAMPLE 3

N-Benzyl-N-methyl-N'-(3-methylthiazolin-2-ylidene)-N"-phenylguanidine, mpt 114°–115.5°, purified by column chromatography on silica using diethyl ether as eluent.

EXAMPLES 4–6

The following thioureas were prepared from the appropriate imine and isothiocyanate by an analogous procedure to that described in Example 1(a):

3-(4-Methylphenyl)-1-(3-methylthiazolin-2-ylidene)-2-thiourea, mpt 195°–8°.

3-(4-Chlorophenyl)-1-(3-methylthiazolin-2-ylidene)-2-thiourea, mpt 215°–7°.

3-(4-Fluorophenyl)-1-(3-methylthiazolin-2-ylidene)-2-thiourea, mpt 178°–9°.

Reaction of these thioureas with iodomethane by an analogous procedure to that described in Example 1(b) gave the following 2-methyl-2-thiopseudoureas:

2-Methyl-1-(4-methylphenyl)-3-(3-methylthiazolin-2-ylidene)-2-thiopseudourea hydroiodide, mpt 170°–1°.

1-(4-Chlorophenyl)-2-methyl-3-(3-methylthiazolin-2-ylidene)-2-thiopseudourea hydroiodide, mpt 154°–5°.

1-(4-Fluorophenyl)-2-methyl-3-(3-methylthiazolin-2-ylidene)-2-thiopseudourea hydroiodide, mpt 162°–3°.

Reaction of the appropriate 2-methyl-2-thiopseudourea and amine, by an analogous procedure to that described in Example 1(c), gave the following carboxamidines:

EXAMPLE 4

N'-(4-Methylphenyl)-N-(3-methylthiazolin-2-ylidene)-4-morpholinecarboxamidine hydroiodide, mpt 216°–9° (isopropanol).

EXAMPLE 5

N'-(4-Chlorophenyl)-N-(3-methylthiazolin-2-ylidene)-1-pyrrolidinecarboxamidine, mpt 121°–2°.

EXAMPLE 6

N'-(4-Chlorophenyl)-N-(3-methylthiazolin-2-ylidene)-4-morpholinecarboxamidine, mpt 147°–9° (petroleum ether, bpt 80°–100°).

EXAMPLE 7

N-(3-Methylthiazolin-2-ylidene)-N'-phenyl-4-thiamorpholinecarboxamidine

Thiamorpholine (1.36 ml) was added to phenylisocyanide dichloride (0.93 ml) in tetrahydrofuran (30 ml) at 0° C., stirred for 30 minutes and filtered. To the filtrate, a solution of 2-imino-3-methylthiazoline (1.55 g) in tetrahydrofuran (30 ml) was added and the mixture allowed to stand for two days, filtered and concentrated. Trituration of the residue and recrystallisation from isopropanol gave the product, mpt 185°–6°, of analytical purity.

EXAMPLES 8–16

The following compounds were prepared by a similar procedure to that employed in Example 7:

EXAMPLE 8

N,N-Diethyl-N'-(3-methylthiazolin-2-ylidene)-N"-phenylguanidine mpt 72°–4°.

EXAMPLE 9

N-(3-Ethylthiazolin-2-ylidene)-N'-phenyl-4-morpholinecarboxamidine, mpt 138°–140°, purified by column chromatography on silica using 5% of (33% dimethylamine in ethanol) in dichloromethane as eluent, then recrystallised from isopropanol.

EXAMPLE 10

N-(3,4-Dimethylthiazolin-2-ylidene)-N'-phenyl-4-morpholinecarboxamidine, mpt 88°–90°, (petroleum ether, bpt 60°–80°).

EXAMPLE 11

N-(3,5-Dimethylthiazolin-2-ylidene)-N'-phenyl-1-pyrrolidinecarboxamidine, mpt 109°–110° (petroleum ether, bpt 60°–80°).

EXAMPLE 12

N-(3,5-Dimethylthiazolin-2-ylidene)-N'-phenyl-4-morpholinecarboxamidine, mpt 101°–4°.

EXAMPLE 13

N'-Phenyl-N-(3,4,5-trimethylthiazolin-2-ylidene)-4-morpholinecarboxamidine, mpt 129°–130° (petroleum ether, bpt 60°–80°).

EXAMPLE 14

N-(5-Bromo-3-methylthiazolin-2-ylidene)-N'-phenyl-4-morpholinecarboxamidine hydrochloride, mpt 133°–5° (ethyl acetate-methanol).

EXAMPLE 15

N-(3-Methylbenzothiazolin-2-ylidene)-N'-phenyl-1-pyrrolidinecarboxamidine, mpt 147°–9°, (petroleum ether, bpt 60°–80°).

EXAMPLE 16

N-(3-Methylbenzothiazolin-2-ylidene)-N'-phenyl-4-morpholinecarboxamidine hydrochloride, mpt 209°–210° (isopropanol-acetone).

EXAMPLE 17

N-(3-Methyloxazolin-2-ylidene)-N'-phenyl-4-morpholinecarboxamidine hydroiodide

Morpholine (0.23 g, 0.23 ml) was added to a stirred solution of phenylisocyanide dichloride (0.23 g, 0.18 ml) in tetrahydrofuran (30 ml), stirred for one hour and filtered. The filtrate was added to a mixture of 2-imino-3-methyloxazoline hydroiodide (0.3 g) and triethylamine (0.53 g, 0.74 ml) in tetrahydrofuran (30 ml), stirred for two days and filtered. The filtrate was evaporated to dryness, the residue triturated with isopropanol and the resultant solid recrystallised from isopropanol then methanol-diethyl ether to give the product, mpt 190°–2°, as its analytically pure hydroiodide salt.

EXAMPLE 18

N,N-Dimethyl-N'-(3-methylthiazolin-2-ylidene)-N"-phenylguanidine hydroiodide, mpt 185°–8° (isopropanol) was prepared by a similar procedure to that described in Example 17.

EXAMPLE 19

N'-(4-Fluorophenyl)-N-(3-methylthiazolin-2-ylidene)-4-morpholinecarboxamidine, mpt 70°–3°, purified by column chromatography on silica using 2% of (33% dimethylamine in ethanol) in dichloromethane as eluent, was prepared by an analogous procedure to that described in Example 1(c).

EXAMPLES 20–22

The following compounds were prepared by an analogous procedure to that described in Example 17:

EXAMPLE 20

N'-(2,6-Dichlorophenyl)-N-(3-methylthiazolin-2-ylidene)-4-morpholinecarboxamidine, mpt 131°–2° (isopropanol).

EXAMPLE 21

N-(5-Chloro-3-methylthiazolin-2-ylidene)-N'-phenyl-4-morpholinecarboxamidine, mpt 86°–8°.

EXAMPLE 22

N-(4-Carboethoxy-3-methylthiazolin-2-ylidene)-N'-phenyl-4-morpholinecarboxamidine, mpt 109° (isopropanol).

Biological Data

Activity on Glucose Tolerance in Fasted Mice

For this assay mice were fasted for 24 hours before the experiment and then randomised so that each treatment group contained 8 mice. The compounds were dosed orally in 1% aqueous carboxymethyl cellulose (10 ml/kg body weight), and 30 minutes later glucose (1 g/kg) was administered by the sub-cutaneous route. Blood samples for glucose analysis were taken from the tail 60 minutes after glucose administration; the results are shown in the table below.

N.B.

A standard system for indicating the significance of results with respect to the controls (dose=zero mmol/kg) which received the 1% aqueous carboxymethyl cellulose vehicle only, is as follows:

**P<0.05
***P<0.01
****P<0.001.

In the following Table, column A represents the dose of compound (mmol/kg body weight) and column B represents the blood glucose concentration (mmol/liter) 60 minutes after sub-cutaneous glucose load.

TABLE

| Compound | A | B |
|---|---|---|
| Example 1 | 0 | 5.95 |
|  | 0.25 | 3.24**** |
| Example 2 | 0 | 5.85 |
|  | 0.25 | 3.69*** |
| Example 3 | 0 | 5.47 |
|  | 0.25 | 4.13*** |
| Example 4 | 0 | 5.84 |
|  | 0.2 | 4.44** |
| Example 5 | 0 | 7.44 |
|  | 0.0625 | 4.85*** |
| Example 6 | 0 | 6.53 |
|  | 0.2 | 4.41*** |
| Example 7 | 0 | 7.01 |
|  | 0.2 | 4.77 |
| Example 8 | 0 | 8.60 |
|  | 0.072 | 3.89*** |

TABLE-continued

| Compound | A | B |
|---|---|---|
| Example 9 | 0 | 6.32 |
| | 0.2 | 4.70** |
| Example 10 | 0 | 7.72 |
| | 0.2 | 5.56 |
| Example 11 | 0 | 7.20 |
| | 0.2 | 4.61*** |
| Example 12 | 0 | 7.72 |
| | 0.2 | 3.20 |
| Example 13 | 0 | 5.39 |
| | 0.2 | 3.36** |
| Example 14 | 0 | 6.56 |
| | 0.2 | 5.48 |
| Example 15 | 0 | 5.47 |
| | 0.25 | 4.22*** |
| Example 16 | 0 | 7.15 |
| | 0.2 | 5.55*** |
| Example 17 | 0 | 5.28 |
| | 0.2 | 3.46*** |
| Example 18 | 0 | 6.18 |
| | 0.2 | 3.64*** |

I claim:

1. A method for the treatment of diabetes in humans which comprises administering to the humans a therapeutically effective amount of an active compound of formula (II) or a pharmaceutically acceptable acid addition salt thereof:

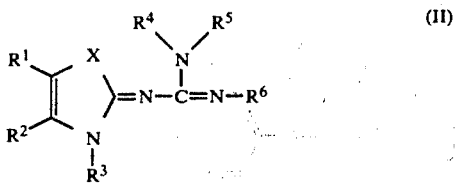

(II)

wherein X represents oxygen or sulphur; $R^1$ and $R^2$ are the same or different and represent hydrogen, halogen, $C_{1-6}$ alkyl, phenyl, benzyl, $C_{3-6}$ cycloalkyl, carbo-$C_{1-6}$ alkoxy or carboxy or $R^1$ and $R^2$ represent the remaining members of a benzene ring; $R^3$ represents $C_{1-6}$ alkyl, phenyl or benzyl; $R^4$ represents $C_{1-6}$ alkyl; $R^5$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^4$ and $R^5$ together represent the remaining members of a 5- or 6-membered ring optionally containing an oxygen, sulphur or additional nitrogen atom and being optionally substituted with $C_{1-6}$ alkyl; and $R^6$ represents $C_{1-6}$ alkyl, phenyl, optionally substituted with up to 3 groups selected from halogen, nitro-, amino-, trifluoromethyl, $C_{1-6}$ alkyl and $C_{1-6}$ alkoxy; or benzyl optionally substituted with up to 3 groups selected from halogen, $C_{1-6}$ alkyl and $C_{1-6}$ alkoxy.

2. A method for the treatment of diabetes in humans which comprises administering to the humans a therapeutically effective amount of an active compound selected from the following, or their pharmaceutically acceptable acid addition salts, N-(3-methylthiazolin-2-ylidene)-N'-phenyl-1-pyrrolidine-carboxamidine; N-(3-methylthiazolin-2-ylidene)-N'-phenyl-4-morpholinecarboxamidine; N-benzyl-N-methyl-N'-(3-methylthiazolin-2-ylidene)-N''-phenylguanidine; N'-(4-methylphenyl)-N-(3-methylthiazoline-2-ylidene)-4-morpholinecarboxamidine; N'-(4-chlorophenyl)-N-(3-methylthiazolin-2-ylidene)-1-pyrrolidinecarboxamidine; N'-(4-chlorophenyl)-N-(3-methylthiazolin-2-ylidene)-4-morpholinecarboxamidine; N-(3-methylthiazolin-2-ylidene)-N'-phenyl-4-thiamorpholinecarboxamidine; N,N-diethyl-N'-(3-methylthiazolin-2-ylidene)-N''-phenylguanidine; N-(3-ethylthiazolin-2-ylidene)-N'-phenyl-4-morpholinecarboxamidine; N-(3,4-dimethylthiazolin-2-ylidene)-N'-phenyl-4-morpholinecarboxamidine; N-(3,5-dimethylthiazoline-2-ylidene)-N'-phenyl-1-pyrrolidinecarboxamidine; N-(3,5-dimethylthiazoline-2-ylidene)-N'-phenyl-4-morpholinecarboxamidine; N'-phenyl-N-(3,4,5-trimethylthiazolin-2-ylidene)-4-morpholinecarboxamidine; N-(5-bromo-3-methyl-thiazolin-2-ylidene)-N'-phenyl-4-morpholinecarboxamidine; N-(3-methyl-4,5-benzothiazolin-2-ylidene)-N'-phenyl-4-morpholinecarboxamidine; N-(3-methylthiazolin-2-ylidene)-N'-phenyl-4-morpholinecarboxamidine; N,N-dimethyl-N'-(3-methylthiazolin-2-ylidene)-N''-phenylguanidine; N'-(4-fluorophenyl)-N-(3-methylthiazolin-2-ylidene)-4-morpholinecarboxamidine; N'-(2,6-dichlorophenyl)-N-(3-methylthiazolin-2-ylidene)-4-morpholinecarboxamidine; N-(5-chloro-3-methylthiazolin-2-ylidene)-N'-phenyl-4-morpholinecarboxamidine; N-(4-carboethoxy-3-methylthiazolin-2-ylidene)-N'-phenyl-4-morpholinecarboxamidine.

* * * * *